US00PP16014P3

(12) United States Plant Patent
Davidson

(10) Patent No.: US PP16,014 P3
(45) Date of Patent: Oct. 4, 2005

(54) FLORIBUNDA ROSE PLANT NAMED 'HADCUP'

(50) Latin Name: *Rosa hybrida*
Varietal Denomination: HADCUP

(76) Inventor: Harvey D. Davidson, 3 El Verano Rd., Orinda, CA (US) 94563

( * ) Notice: Subject to any disclaimer, the term of this patent is extended or adjusted under 35 U.S.C. 154(b) by 208 days.

(21) Appl. No.: 10/700,232

(22) Filed: Nov. 4, 2003

(65) Prior Publication Data

US 2005/0097644 P1 May 5, 2005

(51) Int. Cl.[7] ..... A01H 5/00

(52) U.S. Cl. ..... Plt./145

(58) Field of Search ..... Plt./145, 134

*Primary Examiner*—Howard J. Locker

(57) ABSTRACT

A new and distinct rose cultivar of the Floribunda class characterized by having long lasting clusters of deep yellow flowers on clean stems without prickles and having a rapid rebloom cycle. The plant is upright and bushy and is of medium height, generally averaging about 1 meter. Stems are well covered with matte foliage. The plant is resistant to mildew, rust and blackspot.

1 Drawing Sheet

Botanical/commercial classification: *Rosa hybrida*/Floribunda Rose Plant.

The present invention relates to a new and distinctive cultivar of rose plant of the Floribunda class, which was originated by my crossing 'Kika' as the seed parent with the unamed seedling ((Basildon Bond×Arthur Bell)×Midas Touch)) as the pollen parent. The cultivar name of this plant is designated as 'Hadcup'. It is being marketed under the commercial name of 'Smooth Buttercup'.

Among the novel characteristics possessed by the new cultivar which distinguish it from:

(a) All other cultivars of which I am aware are:

(1) Prickles are absent from any stems.

(2) Deep yellow flowers.

(3) Flowers in clusters of 3 to 14 blooms.

(4) Very consistent free bloomer.

(b) Seed parent: White hybrid tea, few prickles.

Pollen parent: Medium yellow floribunda with prickles. Asexual reproduction of the new rose cultivar by budding onto the rootstock 'Dr. Huey', as performed at Wasco, Calif., shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aforementioned color chart, e.g. 'Yellow Group 16A' in Fan 1 of The Royal Horticultural Society Colour Chart.

Parentage:

*Seed parent.*—IRAR registered: 'Ortkee'; commercial name: 'Kika'; Not patented.

*Pollen parent.*—Unnamed seeding — ((Basildon Bond×Arthur Bell)×Midas Touch)).

Class: Floribunda.

The following observations are made of specimens grown outdoors in Orinda, Contra Costa County, Calif., in the month of October, 2003.

FLOWER

Blooming habit:

A. Bud:

(*1*) *Size.*—Sepals enclosed, 20–22 mm from base of sepals to top of bud.

(*2*) *Form.*—Ovoid.

(*3*) *Sepals.*—30 to 35 mm in length; 6 to 8 mm extension beyond bud; no serration shown on sepal edges. Generally 3 out of 5 sepals show appendages on each side, 3 to 5 mm length. Sepals show glandular development on edges. Heavy cotton matting on inner surface, fine matting on outer surface. Outside color near to Yellow Green 146B; inside near to Yellow Green 145AC.

(*4*) *Peduncle.*—Length — 5 to 6 cm. Surface — smooth. some fine hairs, no glandular hairs, no prickles. Strength — firm. Color — near Yellow Green 146C.

(*5*) *Receptacle.*—Shape — Oblong, 8–10 mm diameter, Color — same as peduncle.

(*6*) *Color.*—When sepals first divide, outside bud petals near to Yellow Group 13A.

B. Bloom:

(*1*) *Size.*—When open — 6.5 to 7.5 cm.

(*2*) *Borne.*—Per stem clusters of 3 up to 14 per stem.

(*3*) *Form.*—Globular.

(*4*) *Petalage.*—Average — 24 to 26.

(*5*) *Color.*—Early open: outside and inside of outer petals Yellow Group 13A, base and inside petals same. Aging: petals near to Yellow Group 13C, base 13D.

C. Petals:

(*1*) *Texture.*—Firm.

(*2*) *Appearance.*—Flexed; satiny.

(*3*) *Form.*—Ruffled.

(*4*) *Arrangement.*—Semi regular.

(*5*) *Petaloids in center.*—Average 6 to 8.

(6) *Persistence.*—Petals hold well, drop cleanly.
(7) *Fragrance.*—Moderate.
(8) *Lasting quality.*—On the plant about 10–12 days; as cut flower about 6–8 days.

REPRODUCTIVE ORGANS

A. Stamen:
(1) *Arrangement.*—Regular around styles.
(2) *Number.*—Average 110–120.
(3) *Length.*—Average — 6 to 10 mm.
(4) *Filaments.*—Color — Close to Yellow Orange Grp. 15A.
(5) *Anthers.*—Color — Close to Yellow Orange Group 15A.
(6) *Pollen.*—Color — Close to Yellow Orange Group 15A.

B. Pistil:
(1) *Styles.*—Length: 6–12 mm from center of ovary; number 50–55; color: near to Red Grp. 41C; sparsley coated with white hairs.
(2) *Stigma.*—Color — Close to Yellow Grp. 10B.
(3) *Ovary.*—Shape — oblong; 7–9 mm center cross section at sepal base.

C. Hips: Few hips but will set seed. Mature hip: Size: 1½–2 cm; Shape: Round Color: Orange Grp. 25A.

PLANT

A. Form: Upright.
B. Growth: Vigorous, Height: 70–80 cm; Width: 45–55 cm.
C. Stem length: Basal break to flower bud tip: average 75–80 cm.
D. Foliage: Compound of 3 to 5 leaflets on bloom stem; 5 to 7 leaflets on main canes.
(1) *Mature size.*—5 leaflet — tip of leaflet to stipule base 12–13 cm.
(2) *Quantity.*—Stems well covered.
(3) *Color.*—New foliage upper side near to Yellow Green 146B with shades of Greyed Orange 176C; under side near to Yellow Green 146A shaded Greyed Orange 176B. Old foliage upper side near to Yellow Green 147A; under side near to Yellow Green 146B.
(4) *Shape.*—Oval with center pointed.
(5) *Texture.*—Firm, leathery, matte finish.
(6) *Edge.*—Serrated on outer edge. Average 5 to 6 points per 1 cm, with up to 1 mm peak.
(7) *Rachis.*—Glandular hairs on lower and upper side; few prickles on lower side, 1 mm length.
(8) *Stipules.*—Length 15–18 mm; auricle to 3–4 mm. Edge of stipule to tip of auricle with few glandular hairs.

E. Resistance to disease: Powdery mildew, rust and black-spot: Good.
F. Wood:
*New wood.*—Color close to Yellow Green 146C; Bark — smooth.
*Old wood.*—Color close to Yellow Green 146B; Bark — smooth.
G. Prickles: None.
H. Winter hardiness: Average.

I claim:

1. A new and distinct rose cultivar of the Floribunda class, characterized in particular by prickles being absent from any stems, deep butter yellow colored flowers borne in clusters of up to 14 flowers, and rapid rebloom cycle, substantially as herein shown and described.

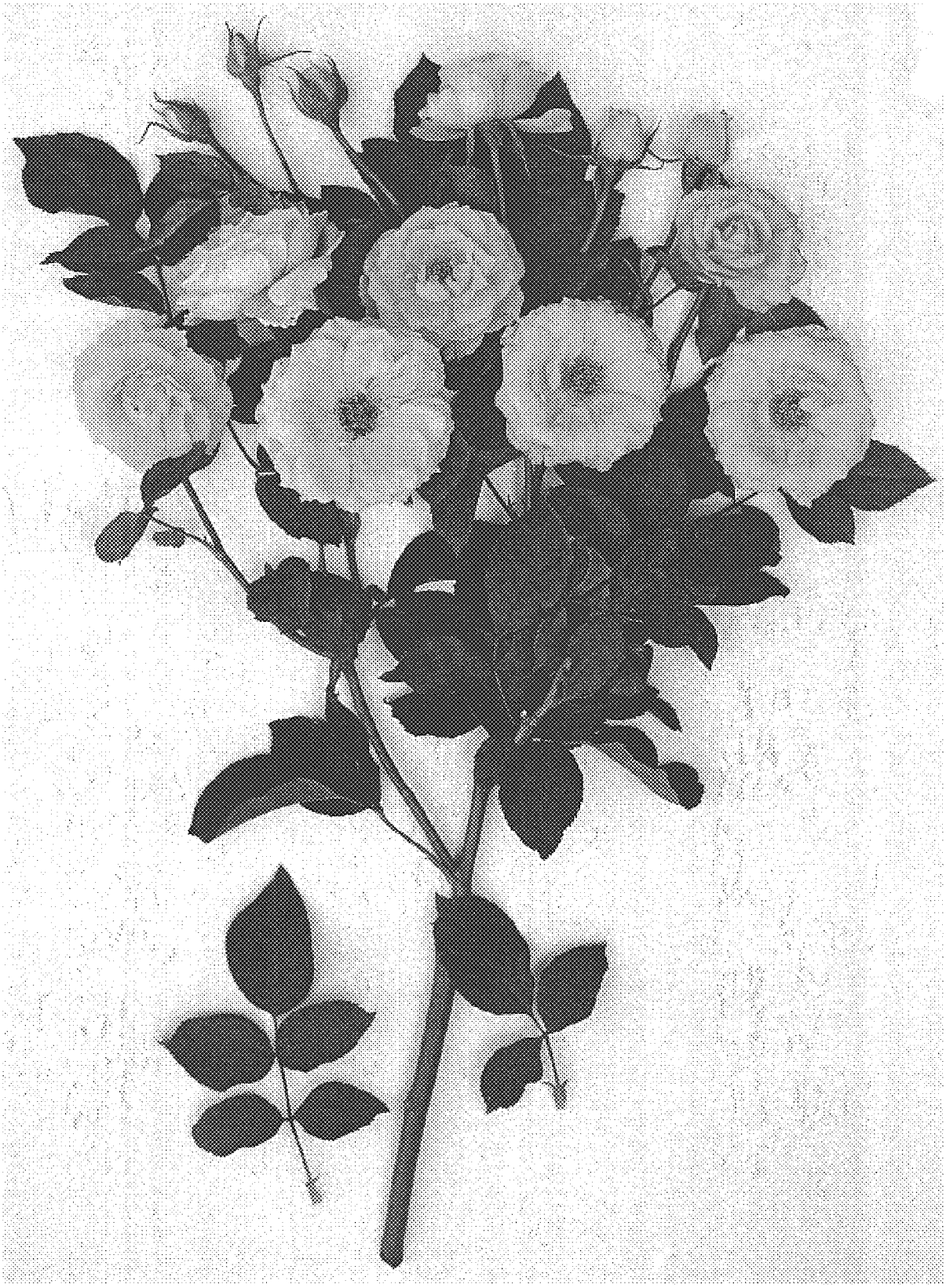

* * * * *